US005948610A

United States Patent [19]

Ho et al.

[11] Patent Number: 5,948,610

[45] Date of Patent: Sep. 7, 1999

[54] USE OF MATRICES COMPRISING LIQUIDS AND LIGHT ABSORBING PARTICLES FOR ANALYSIS OF MICROORGANISMS BY LASER DESORPTION MASS SPECTROMETRY

[75] Inventors: Yen-Peng Ho, Ellicott City; Catherine Fenselau, Baltimore, both of Md.

[73] Assignee: University of Maryland at Baltimore County, Balitmore, Md.

[21] Appl. No.: 09/133,742

[22] Filed: Aug. 13, 1998

Related U.S. Application Data

[60] Provisional application No. 60/087,811, Jun. 3, 1998.

[51] Int. Cl.$^{6}$ .............................. C12Q 1/00; C12Q 1/04; G01N 33/92

[52] U.S. Cl. ................................ 435/4; 435/34; 435/847; 435/848; 435/849; 436/71; 436/13; 436/173

[58] Field of Search ................................ 435/4, 34, 847, 435/848, 849; 436/71, 13, 173

[56] References Cited

U.S. PATENT DOCUMENTS 5,059,527 10/1991 White et al. ............................ 435/34

OTHER PUBLICATIONS

Bargiota et al; Int. J. Food Microb; vol. 4(3) pp. 257–266; (1987) (Abstract) Month Not Available.

*Primary Examiner*—Louise N. Leary
*Attorney, Agent, or Firm*—Benjamin Aaron Adler

[57] ABSTRACT

The present invention is directed to a method of using a liquid matrix containing a black body light absorbing powder to facilitate the analysis of biomarkers from representative microorganisms by laser desorption mass spectrometry. Both an IR laser (1064 nm) and a UV laser (337 nm) were shown to be compatible and both time-of-flight and Fourier-transform mass analyzer were used. In the present implementation gram negative and gram positive bacteria were suspended in a methanol:chloroform solution and added to a cobalt/glycerol matrix, S/N, sensitivity and sampling time are greatly enhanced for polar lipid biomarkers.

6 Claims, 14 Drawing Sheets

$R_1$, $R_2$ = alkyl chains

R =

Phosphatidylethanolamine
(PE)

Phosphatidylglycerol
(PG)

Diglucosyl-diglyceride
(DGDG)

USE OF MATRICES COMPRISING LIQUIDS AND LIGHT ABSORBING PARTICLES FOR ANALYSIS OF MICROORGANISMS BY LASER DESORPTION MASS SPECTROMETRY

CROSS-REFERENCE TO RELATED APPLICATION

This patent application claims benefit of provisional patent application U.S. Ser. No. 60/087,811, filed Jun. 3, 1998, now abandoned.

BACKGROUND OF THE INVENTION

1. Field of the Invention

The present invention relates generally to the fields of analytical chemistry and biochemistry. More specifically, the present invention relates to using matrices comprising viscous liquids and light absorbing particles for analysis of microorganisms by laser desorption mass spectrometry.

2. Description of the Related Art

In the last decade, matrix-assisted laser desorption/ionization (MALDI) has become one of the most important ionization method used for biological mass spectrometry.[1-3] Before the invention of matrix-assisted laser desorption/ionization, several desorption techniques had been used to produce ions. These include field desorption,[4] plasma desorption,[5] laser desorption,[6] SIMS[7] and fast atom bombardment (FAB).[8] Most important is the introduction of the liquid matrix in FAB, opening up a new era of biochemical applications of mass spectrometry.

The requirements for a matrix-assisted laser desorption/ionization matrix include absorption of the laser light, promotion of ionization and dispersion of the energy deposited on the sample in order to produce intact analyte ions. A useful matrix would also be compatible with a broad range of laser wavelengths. Further, matrix-assisted laser desorption/ionization experiments are thought to require co-crystallization of analytes with solid matrices such as 2,5-dihydroxybenzoic acid and 4-hydroxy-α-cyanocinnamic acid. There are several problems associated with these crystallization processes. The tendency to form inhomogeneous crystalline phases leads to the existence of "sweet spots". The ion signal also decreases with the number of laser shots impinging on a given sample spot. In contrast, no crystallization process is involved in liquid matrix methods. Analytes are dissolved in the liquid and are evenly distributed. This provides a homogeneous response and extends the sample lifetime at a given spot as the matrix backfills the cavities and dilutes molecules damaged by the laser beam.

Several approaches toward the use of liquids have been made. One approach is the use of laser light-absorbing liquids as matrices. For example, 3-nitrobenzyl alcohol has been evaluated with a 266 nm laser or a $N_2$ laser at 337 nm.[9-11] Glycerol whose O—H stretching mode has strong absorption in the 3 μm region, has been used with IR lasers at 2.94 μm and 10.6 μm to provide mass spectra of lysozyme at 14,300 Da.[12-14] Alternatively, for liquid matrices that do not absorb the laser wavelength, strongly absorbing compounds such as rhodamine 6G (absorbing visible laser light at 532 nm)[15,16] and 2-cyano-5-phenyl-2,4-pentadienoic acid (absorbing UV laser light)[17] has been dissolved in the matrix.

Another similar approach to coupling laser irradiation into liquid matrices is to suspend small particles in the liquids. Tanaka et al. were the first group to report UV-matrix-assisted laser desorption/ionization mass spectra of proteins as large as chymotrypsinogen (~25,700 Da) by suspending 30 nm cobalt particles in glycerol.[18] Recently, Hillenkamp et al. have evaluated various combinations of particles (TiN, Pb, graphite) and solvents (glycerol, 3-nitrobenzylalcohol, triethanolamine, DMSO) to obtain mass spectra of peptides and proteins using a 337 nm and 1064 nm lasers.[19] Sunner et al.[20] and Zenobi et al.[21,22] reported mixing graphite particles with glycerol and diethanolamine. Liquid matrices consisting of glycerol and $K_4[Fe(CN)_6]$ or $Na_4[Fe(CN)_6]$ have been investigated by Allmaier et al.[23,24]

The rapid and accurate characterization of microorganisms is important in many applications including food production, disease diagnoses and biohazard recognition. Fast atom bombardment, which is well known for its use of a liquid matrix has been used worldwide to differentiate bacteria based on profiles of cellular polar lipids.[25-27] Furthermore, spectra of polar lipids may be obtained directly from lysed cells without extraction or processing. The liquid matrices serve a role to separate soluble compounds in microorganisms and to bring the sample to the surface. Using liquid matrices for matrix-assisted laser desorption/ionization, mass spectra of peptides have been obtained that are similar to those obtained by fast atom bombardment.[20]

The prior art is deficient in the lack of application of particle/liquid matrices to improve the use of matrix-assisted laser desorption ionization mass spectrometry and for the detection of different phospholipids and other biomarkers directly from microorganisms on different kinds of mass spectrometers. The present invention fulfills this long-standing need and desire in the art.

SUMMARY OF THE INVENTION

The rapid and accurate characterization of microorganisms is important in many applications such as food production, disease diagnoses and biohazard recognition. In the last decade, matrix-assisted laser desorption/ionization has become one of the most important ionization methods used for biological mass spectrometry. In general, matrix-assisted laser desorption/ionization experiments involve co-crystallization of analytes with solid matrices such as 2,5-dihydroxybenzoic acid and 4-hydroxy-α-cyanocinnamic acid. The use of solid matrices has several problems associated with crystallization processes. The tendency to form inhomogeneous crystalline phases lead to the existence of "sweet spot". The ion signal also decreases with the number of laser shots on a given sample spot. Further, solid matrix does not serve to separate soluble compounds from complex mixtures, such as microorganisms.

Using liquid matrices may circumvent these problems. The present invention is directed to a method using matrices comprising liquids and light absorbing particles with laser desorption mass spectrometry to analyze microorganisms. Specifically, liquid glycerol with cobalt powder or graphite powder is used as a matrix.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the matrix-assisted laser desorption/ionization mass spectra of substance P using a glycerol matrix.

FIG. 2 shows the Laser desorption/ionization mass spectra of substance P mixed with cobalt particles.

FIG. 3 shows the Laser desorption/ionization mass spectra of substance P using a glycerol/cobalt matrix.

FIG. 6 shows matrix-assisted laser desorption/ionization mass spectra of *Bacillus thuringiensis.

DETAILED DESCRIPTION OF THE INVENTION

Figure 1A:
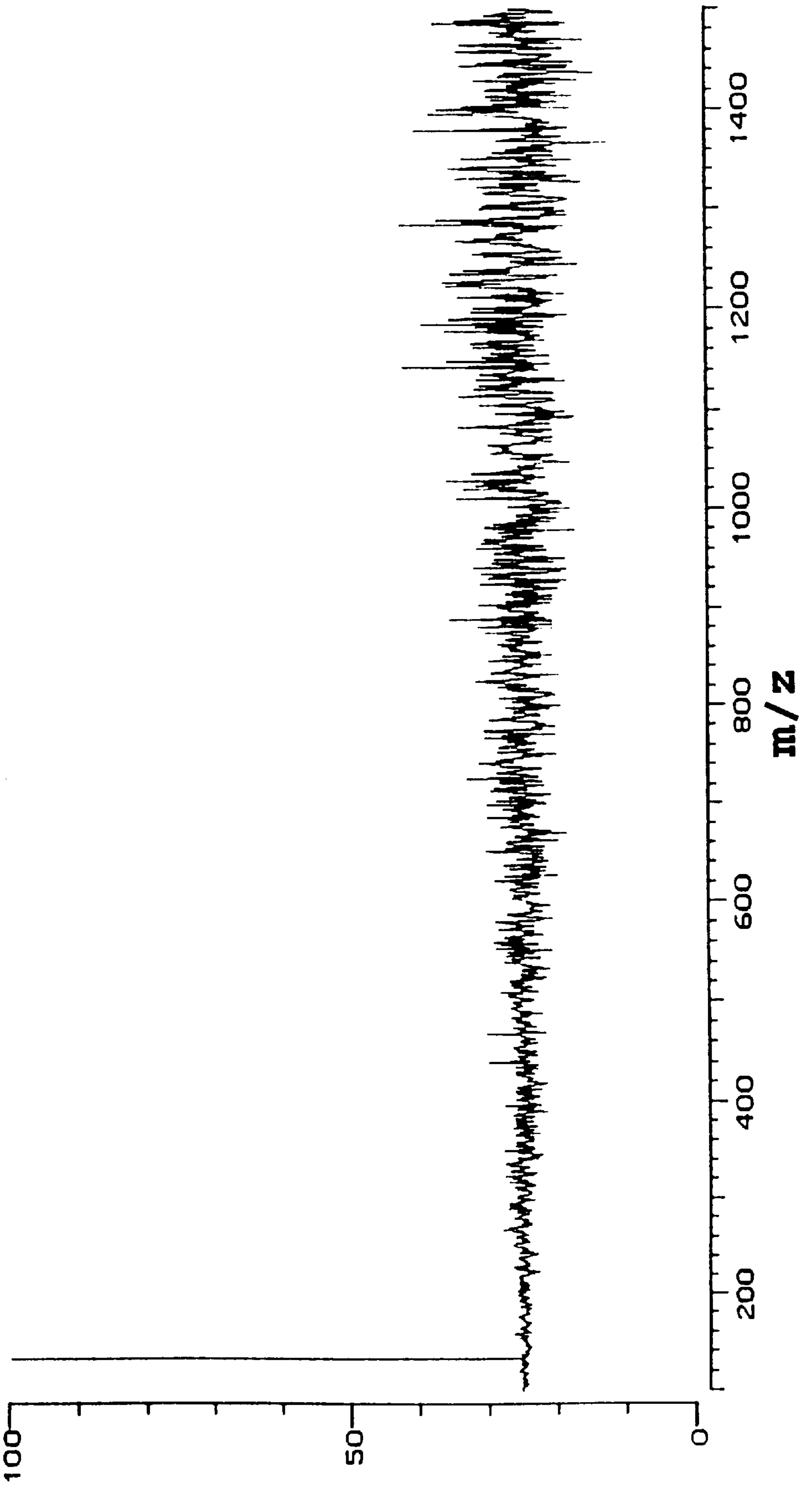
FIG. 1A shows the spectrum with the addition of cobalt particles.

Glycerol has been used as the matrix in fast atom bombardment (FAB) where it allows continual replenishing of the sample at the surface and allows ionization to be enhanced by addition of acid or base. In contrast to solid matrix methods where analytes co-crystallize with the matrices, no crystallization process is involved in liquid matrix methods. Analytes are dissolved in the liquid and are evenly distributed. This circumvents the "sweet spot" problem in solid matrix methods. Sample lifetime at a given spot is extended due to the flowing nature of the liquid matrix. Furthermore, phosphatidylethanolamine (PE) and phosphatidylglycerol (PG) are two of the major lipids found in microorganisms. When they are analyzed in a standard mixture or in a bacterial sample, the conventional solid matrix-assisted laser desorption method discriminates against phosphatidylglycerol. However, when glycerol/cobalt was used as a matrix, both phosphatidylethanolamine and phosphatidylglycerol could be detected from an equimolar mixture of standards with equal sensitivities.

Quantization within mixtures is improved, since discrimination in the desorption process is reduced or eliminated when glycerol/cobalt is used a matrix. For microorganisms the glycerol matrix separates soluble biomarkers from the cellular structure, thus increasing reproducibility. The liquid character of the glycerol/cobalt matrix increases the number of laser shots on a given spot and improves the signal to noise ratios of averaged spectra without moving the sample or the laser beam. The liquid matrices may also reduce thermal decomposition of analytes during the laser desorption process and maximize molecular ion abundances.

The present invention is directed to a method of using matrices comprising liquids and light absorbing particles for analysis of microorganisms by laser desorption mass spectrometry. Specifically, liquid glycerol with cobalt or graphite particles is used as a matrix for the detection of phospholipids and other biomarkers of microorganisms on different kinds of mass spectrometers and using lasers with different wavelengths.

More specifically, the present invention is directed to a method of detecting biomarkers of microorganisms, comprising the steps of: suspending a microorganism sample in a methanol:chloroform solution; mixing said sample with a matrix comprising liquid(s) and light absorbing particles; and detecting biomarkers in microorganisms by utilizing mass spectrometry to said sample. Preferably, the biomarkers are conjugated lipids. Representative conjugated lipids include phosphatidylethanolamines, phosphatidylglycerols and diglycosyldiglycerides. Preferably, the liquid is glycerol. Representative light absorbing particles are cobalt particles and graphite particles. Preferably, the mass spectrometry laser desorption mass spectrometry, matrix-assisted laser desorption ionization time-of-flight mass spectrometry or matrix-assisted laser desorption ionization Fourier-transform mass spectrometry.

The following examples are given for the purpose of illustrating various embodiments of the invention and are not meant to limit the present invention in any fashion.

EXAMPLE 1

Materials and Methods

The matrix-assisted laser desorption ionization experiments were mostly carried out on an IonSpec Fourier-transform ion cyclotron resonance (FT-ICR) mass spectrometer equipped with a 4.7 Tesla superconducting magnet. Mass spectra were also obtained on a Kratos Analytical Kompact matrix-assisted laser desorption/ionization 4 time of flight (TOF) mass spectrometer. For FT-ICR, samples were deposited on a stainless steel direct-insertion probe and ions were generated by focusing a 6 ns laser light at its fundamental output frequency (1.06 $\mu$m wavelength, Nd:YAG laser, Minilite, Continuum, Inc., Santa Clara, Calif.) onto the sample probe. The ions produced by laser pulses were accelerated out of the source and injected by an rf-only quadrupole ion guide into the FT-ICR analyzer cell. After a delay of about 4 seconds, the ions were accelerated by a chirp excitation waveform and the resulting image current were amplified, digitized and Fourier transformed to produce a mass spectrum. For TOF spectra, a 3 ns nitrogen laser beam was used at a wavelength of 337 nm (VSL-337, Laser Science, Inc., Newton, Mass.) to desorb and ionize analytes. The acceleration voltage was 20 kV. Pulse extraction was activated and the spectra were obtained in the linear and positive ion mode.

Substance P and lipid standards were obtained from Sigma Chem. Co, St. Louis, Mo. Glycerol was obtained from Aldrich Chem. Co., Milwaukee, Wis. Cobalt particles (30 nm) were purchased from Vacuum Metallurgical Co., Japan. Graphite particles (2 μm) were from Aldrich Chem. Co. (Milwaukee, Wis.). *Bacillus thuringiensis* (HD-1), *Bacillus sphaericus, Erwinia herbicola* (ATCC#33243) and *Escherichia coli* (ATCC#11775) were grown in neutral broth with aeration for 24 h at 37° C. Cell cultures were harvested by chilling the culture in an ice water bath followed by centrifugation. After the supernatant was removed, the pelleted cells were washed three times with distilled water and lyophilized.

The matrix was prepared by suspending the cobalt or graphite particles in liquid glycerol. For each analysis, the mixture was vortexed and 0.4 μl of the matrix was applied onto the probe. An equal volume of the analyte solution was subsequently added on top of the matrix. Before being transferred into the source, the sample was in the atmosphere for 2–3 minutes to allow volatile solvent to evaporate and to ensure better mixing of the matrix and the analyte. For bacterial samples, lyophilized cells was added to 1:2 methanol/chloroform to make a 10 mg/ml suspension. The suspension was vortexed for 30 seconds before deposition on the sample holder.

EXAMPLE 2

Results

Figure 1B:
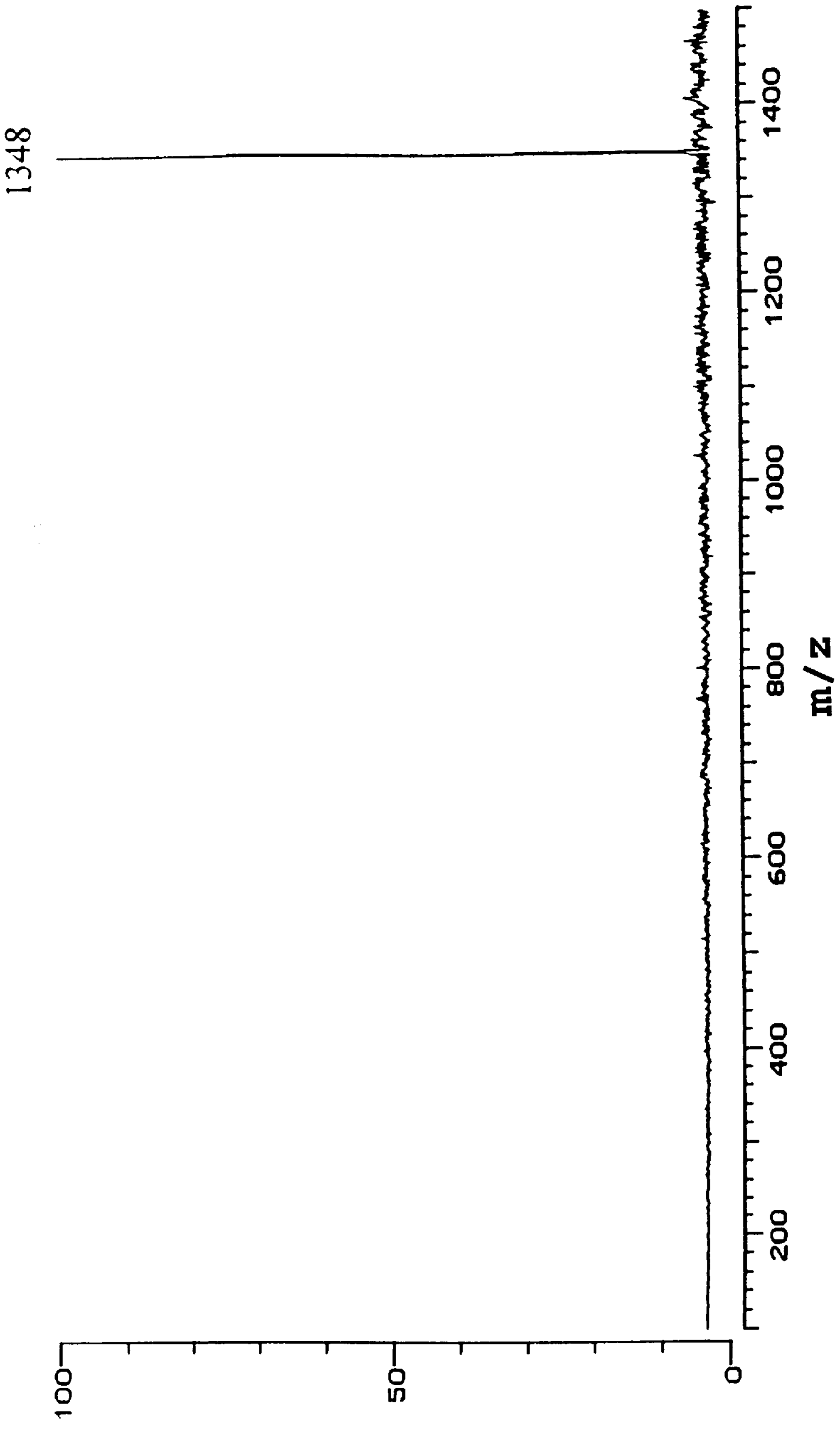
FIG. 1B shows the spectrum without the addition of cobalt particles.

Glycerol can not be used alone as a matrix in matrix-assisted laser desorption/ionization at wavelengths ranging from UV to near IR (1 μm) because it lacks absorption bands in this wavelength region. As shown in FIG. 1A, there was no observable substance P signal when glycerol alone was used as a matrix. FIG. 1B shows that a strong peak corresponding to protonated molecular ions of substance P was observed when cobalt powder was added to the glycerol matrix. It is believed that the mechanism involves the absorption of laser light by the small particles, heat conduction from these particles to the surrounding glycerol liquid and analyte, leading to rapid thermal desorption of analytes. Each particle here acts as a blackbody that absorbs the radiation falling on it. Because of the blackbody property, the mixed matrices may be used with lasers at any wavelength. Ionization is considered to occur by the same combinations of mechanisms defined for fast atom bombardment (FAB).[8]

FIG. 1B also shows a spectrum of substance P obtained from the particle/glycerol matrix. No glycerol clusters or adduct peaks are detected. There are at least two reasons for this. First, a relatively low laser fluence (~100 mJ/$cm^2$) was used. At higher fluences, some adduct peaks with $Na^+$, $K^+$ and chemical background peaks arising from glycerol and cobalt were present (spectrum not shown). Second, an external quadrupole ion guide was used to transfer ions into the FT-ICR cell. The frequency applied to the quadrupole rods is 890 kHz. Ions with m/z values lower than approximately 200 could not be transferred into the cell.

Figure 2A:
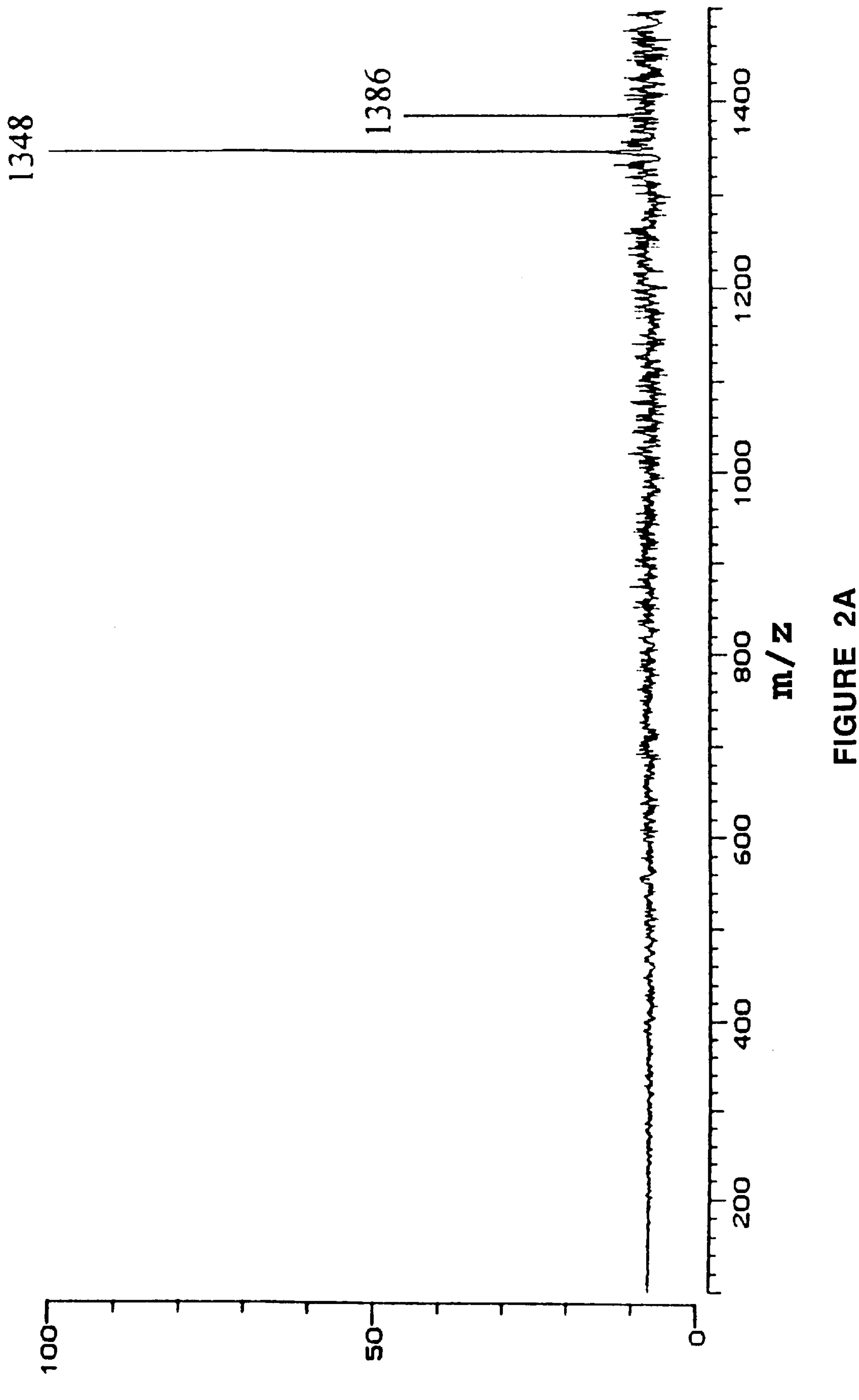
FIG. 2A shows the first 10 shots.
Figure 2B:
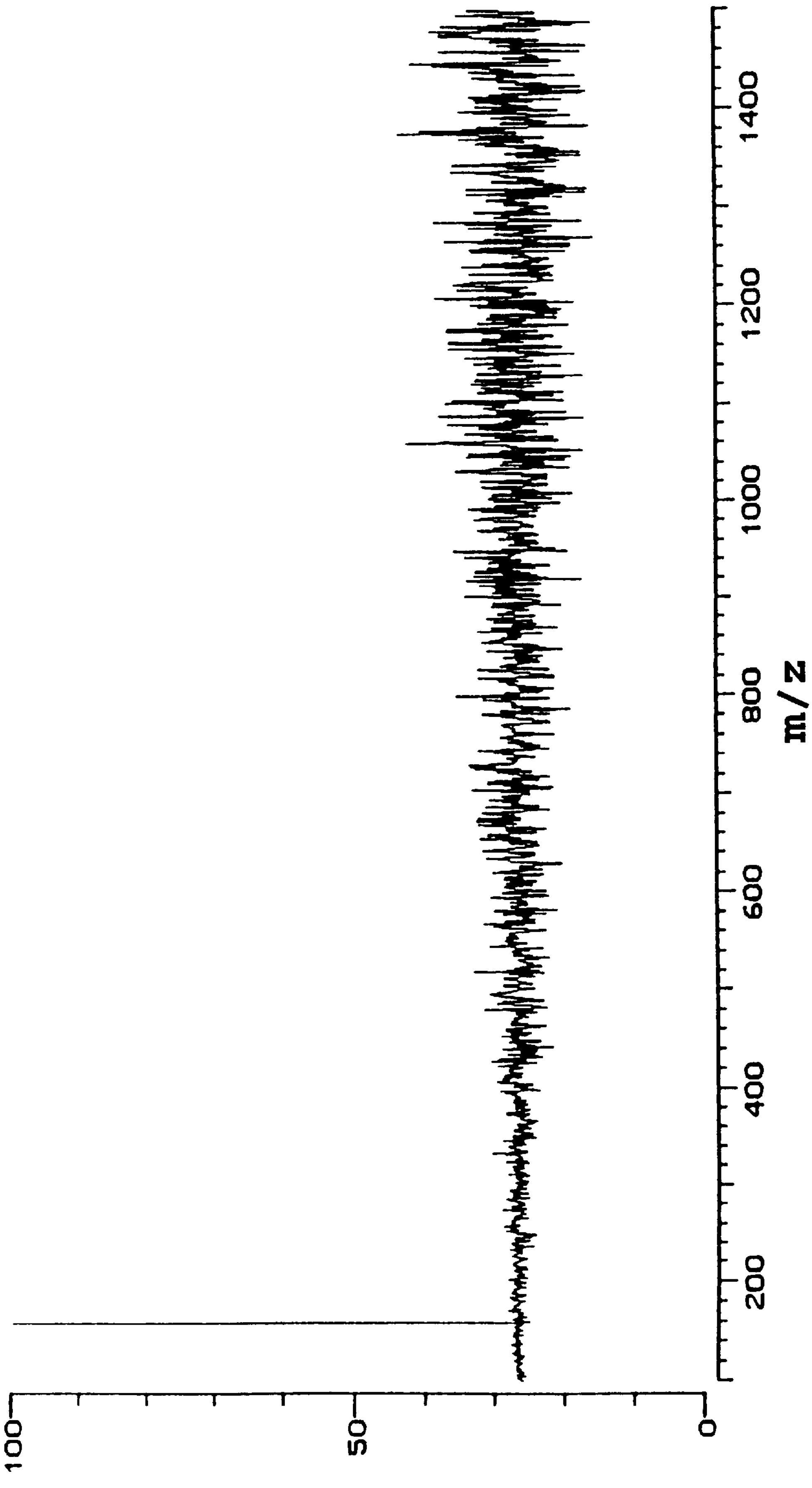
FIG. 2B shows the 11th to 20th shots.

FIG. 2A shows a mass spectrum of substance P desorbed from a dry sample that was prepared by mixing a acetonitrile/water (3:7) solution of substance P with cobalt powder. Both protonated and sodiated molecular ions were detected. However, the sample spot (<1 $mm^2$) was depleted very quickly. FIG. 2B shows that the signal disappears after 10 shots. This problem is circumvented by adding a liquid matrix such as glycerol.

Figure 3A:
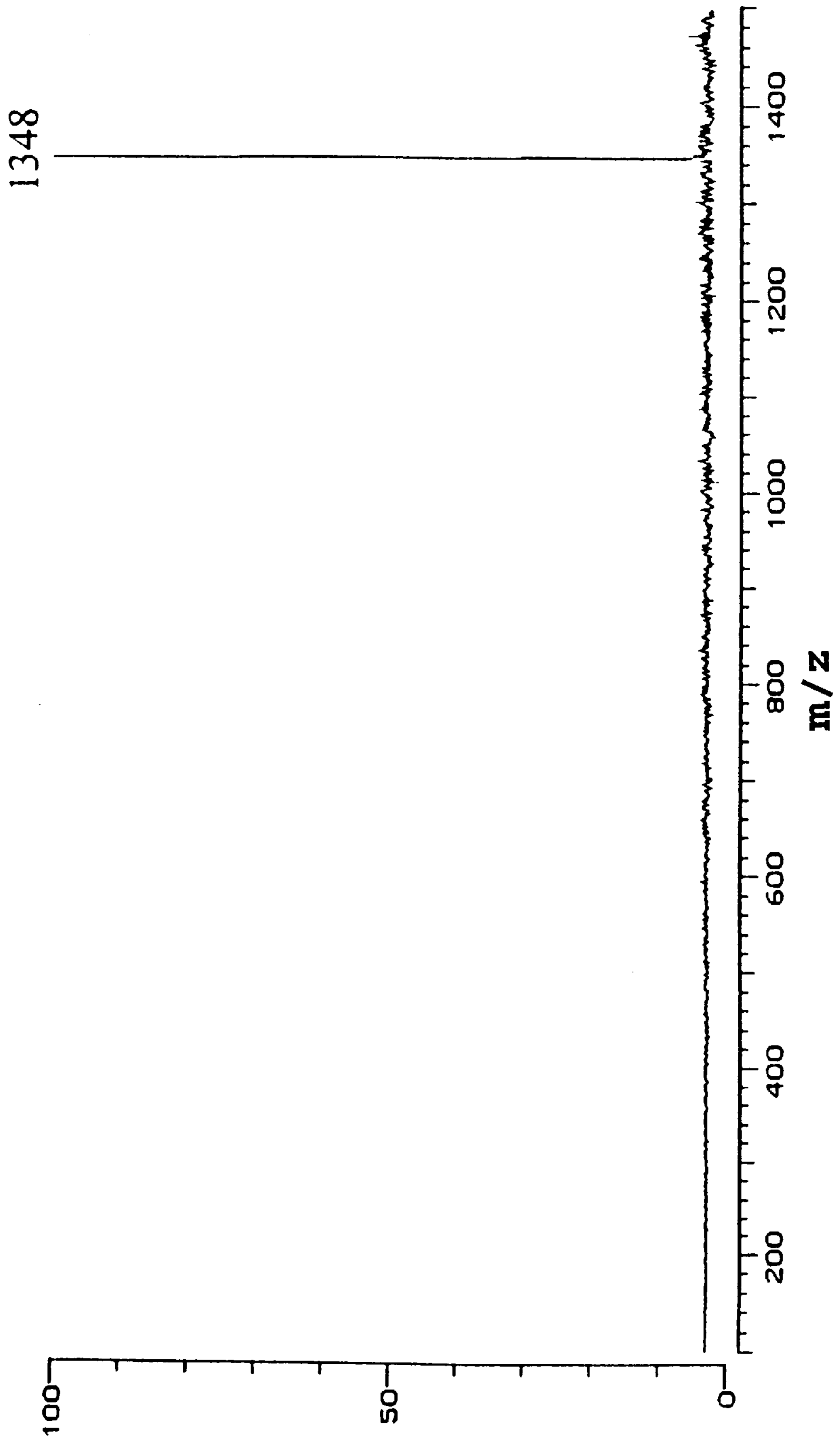
FIG. 3A shows the first 10 shots.
Figure 3B:
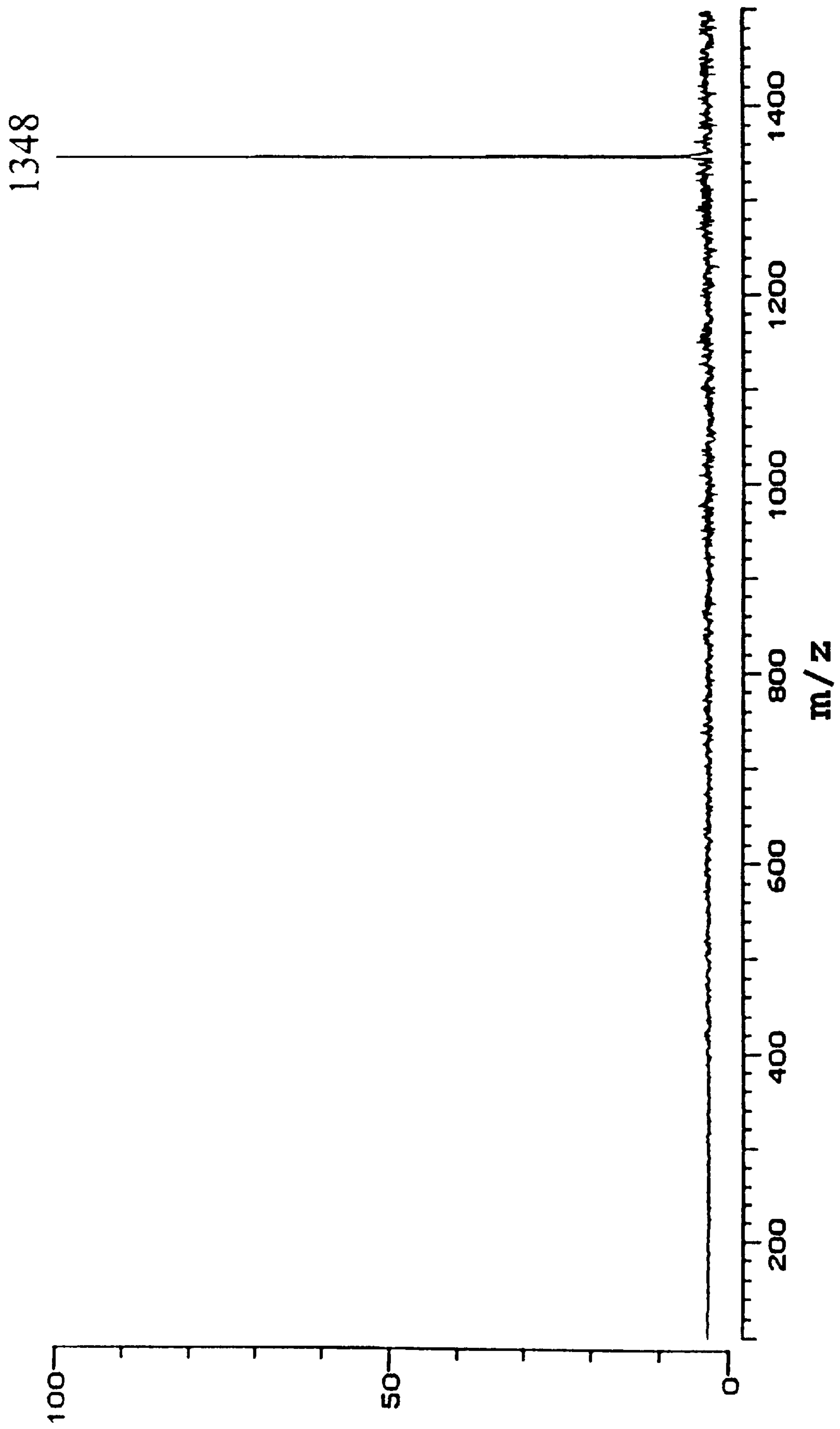
FIG. 3B shows the 90th–100th shots.

The mass spectra of substance P in FIGS. 3A and 3B were obtained by averaging the first 10 shots and the 91st to 100th shots using the Co/glycerol matrix. It is clear that glycerol has an effect analogous to that distinguishing FAB from dry SIMS. Analyte is replenished after each laser shot and the sample lifetime was extended tremendously. The depletion rate depends on the laser power applied to the sample, however, an estimate of the actual laser fluence absorbed by the analyte for two different sample preparations (with and without glycerol) is virtually impossible. The comparison was made by adjusting laser power to give spectra with similar signal to noise ratios for the first 10 shots. An $[M+N]^+$ peak with a signal/noise ratio exceeding 30 was obtained from 7 femtomole of substance P using 20 mg/ml graphite in glycerol.

It would be desirable to use a lower Co/glycerol ratio in order to take full advantage of the flowing nature of glycerol. However, much higher laser power is needed to obtain signals using lower Co/glycerol ratios. Further, when the Co/glycerol ratio was very low (<2 mg/ml) no signal could be obtained even at the highest available power (~20 mJ). Typically, a Co/glycerol ratio of 100 mg/ml was used to maintain fluidity without sacrificing ion production.

Figure 4:
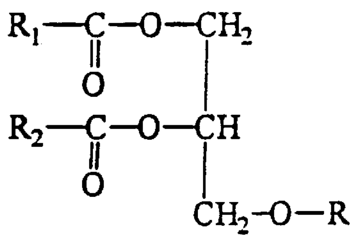
FIG. 4 shows the structures of some polar lipids. The R group is called the polar head group. Shorthand forms are used to indicate the total number of carbon atoms in the two acyl groups of the lipids and the number of unsaturations in these two acyl groups. For example, PE(C30:0) (PE(C31:1)) means that there are total number of 30 (31) carbon atoms and 0 (1) unsaturation in the two acyl groups of phosphatidylethanolamine.
Figure 4:
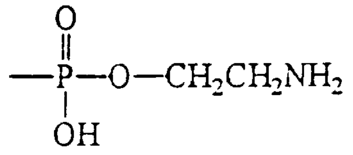
Figure 4:
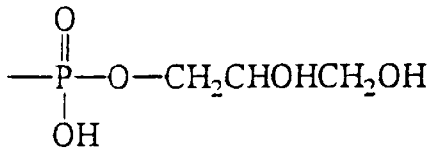
Figure 4:
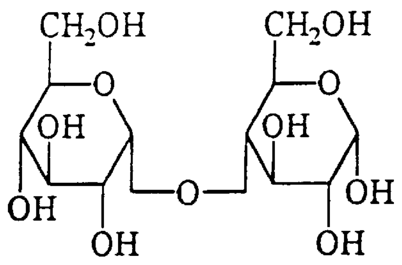
Figure 5:
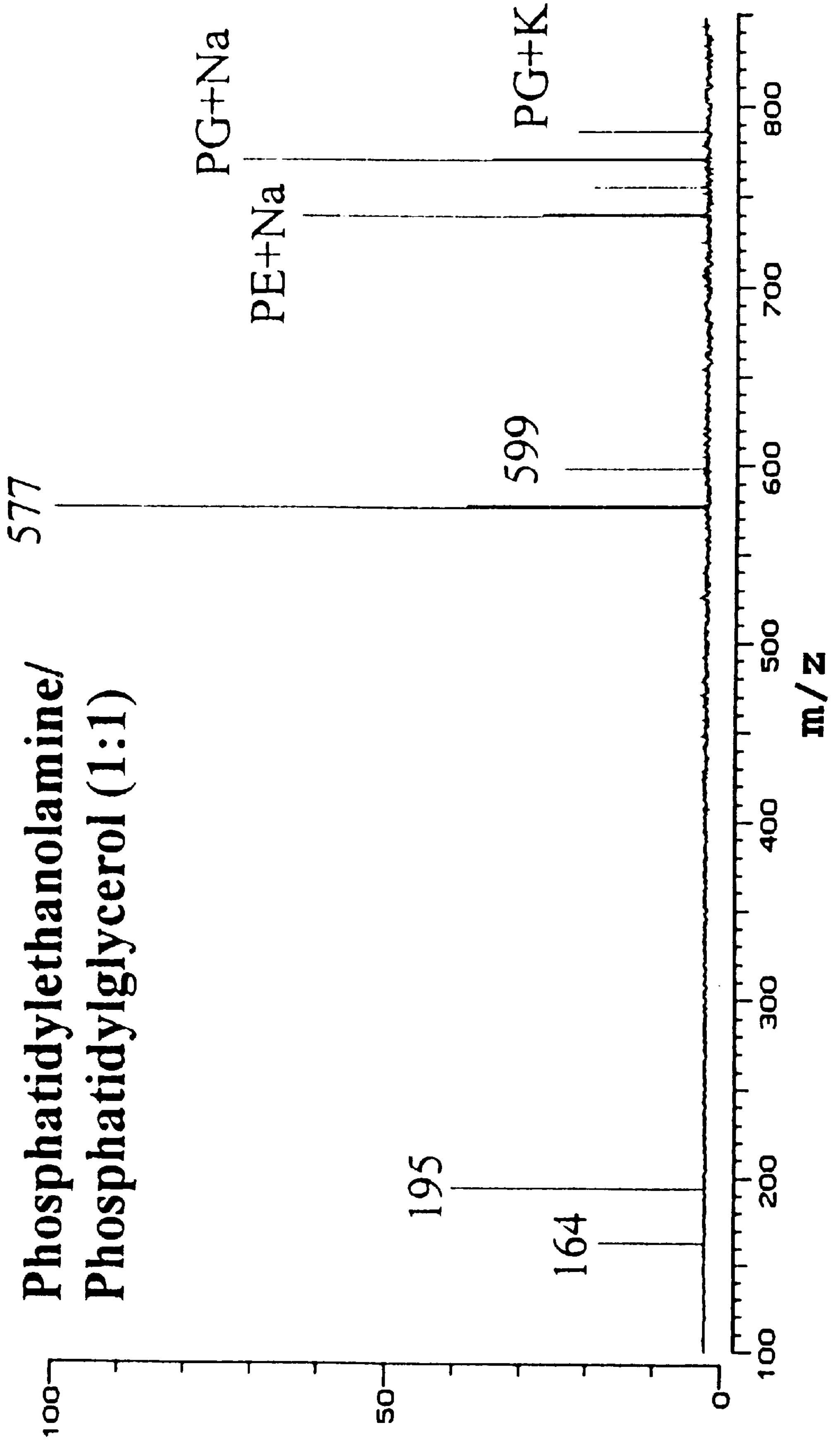
FIG. 5 shows matrix-assisted laser desorption/ionization mass spectrum of PE and phosphatidylglycerol mixture using a glycerol/cobalt matrix.

The Co/glycerol matrix is also suitable for the analysis of phospholipids and other polar lipids. Structures of some of the polar lipids present in bacterial membrane are shown in FIG. 4. FIG. 5 shows a mass spectrum of a 1:1 molar mixture of phosphatidylethanolamine and phosphatidylglycerol. Both sodiated and kaliated molecular ions are detected. Since the phosphatidylethanolamine and phosphatidylglycerol species have the same fatty acid side chains, the masses of fragments arising from polar head group losses are the same, 577 and 599 Da. The peaks at m/z 195, 164 correspond to the sodiated polar head groups of phosphatidylglycerol and phosphatidylethanolamine respectively. No fragments were detected from the weak kaliated phosphatidylglycerol and phosphatidylethanolamine ions.

Figure 6A:
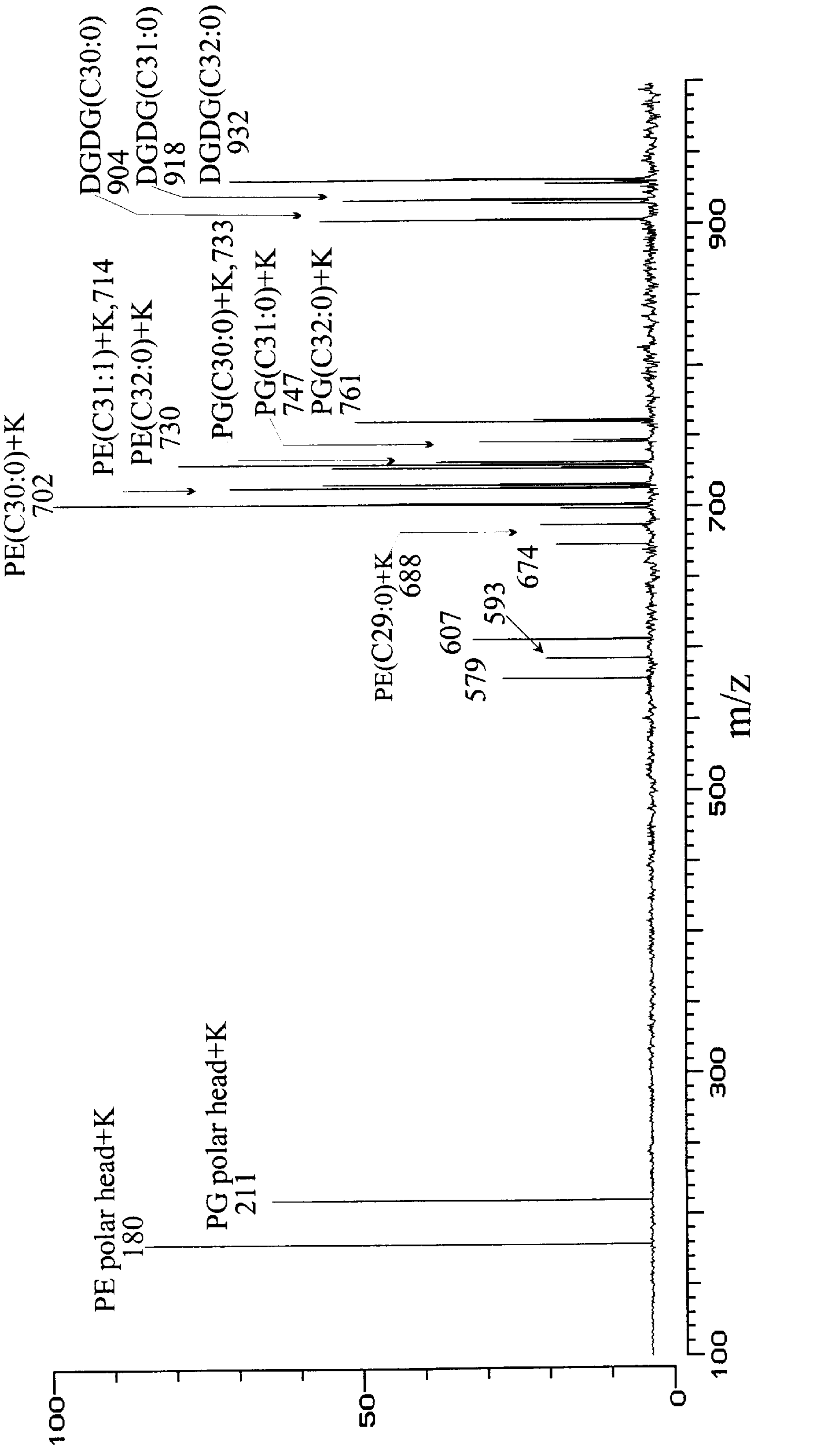
* FIG. 6A shows the full mass spectrum.

Polar lipids were desorbed from samples of two gram positive bacteria, *Bacillus thuringiensis* and *Bacillus sphaericus,* and from samples of two gram negative bacteria, *Erwinia herbicola* and *Escherichia coli* using the cobalt/glycerol matrix. A mass spectrum from *Bacillus thuringiensis* is shown in FIG. 6A. Both phosphatidylethanolamine and phosphatidylglycerol ions were identified (see below). The kaliated polar head group ions occur at m/z 180 and 211. The peaks at m/z 904, 918 and 932 are assigned as kaliated diglycosyldiglyceride (DGDG) (C30:0), (C31:0) and (C32:0) respectively. The peaks at m/z 579, 593 and 607 are, presumably, fragment ions resulting from the loss of the disaccharide moiety from 904, 918 and 932, respectively. It is interesting that the mass spectrum of the pure phospholipid shown in FIG. 5 gives major sodiated products while mass spectra of polar lipids desorbed from bacterial sample mainly contain kaliated molecules. This suggests that more potassium is present in the bacterial sample than in the chemical sample.

Figure 6B:
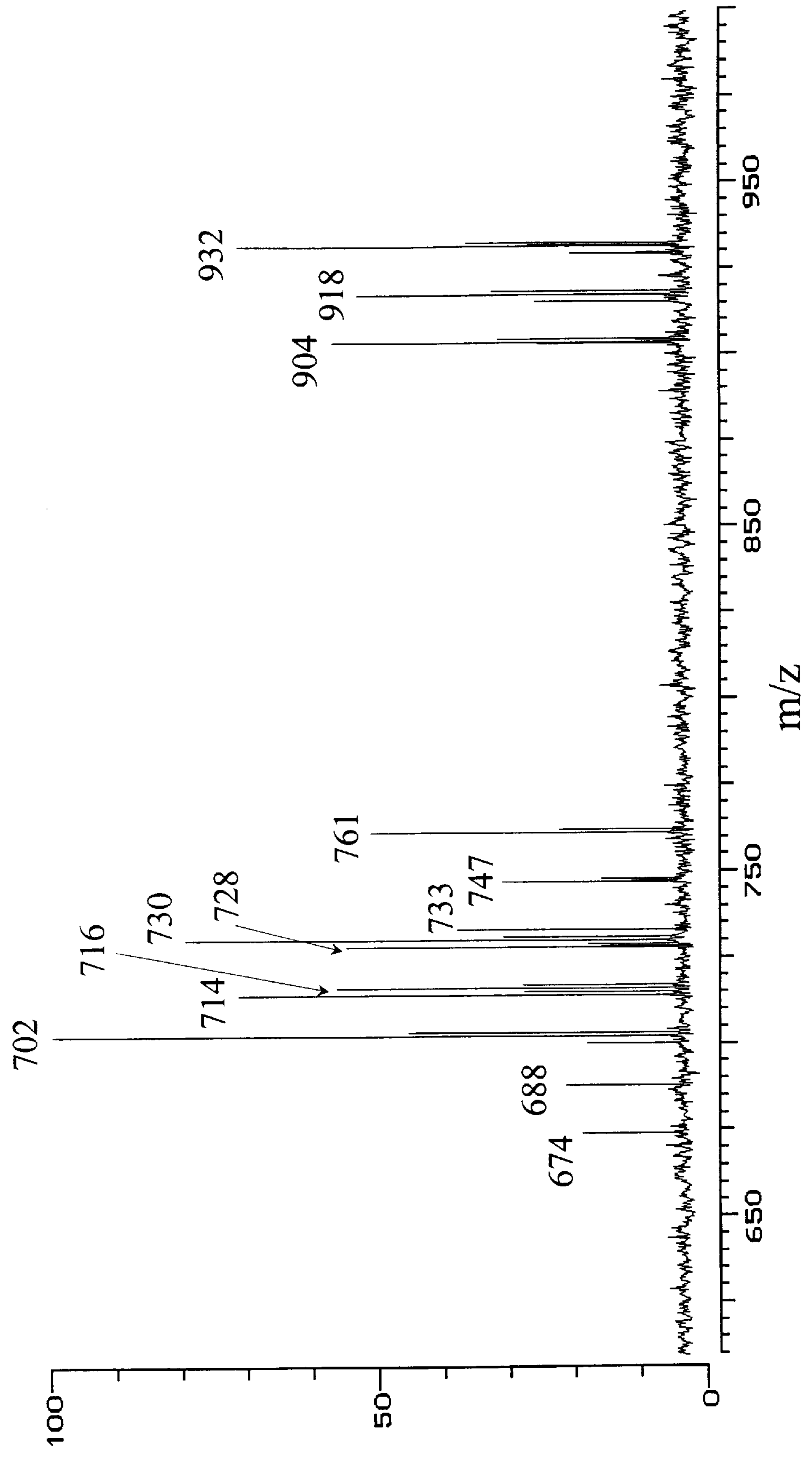
FIG. 6B shows an expansion plot. The spectra were obtained in a Fourier-transform mass spectrometry.

FIG. 6B displays well resolved phosphatidylethanolamine, phosphatidylglycerol and DGDG peaks on an expanded scale from the mass spectrum in FIG. 6A. The heterogeneity characteristic of microorganisms is observed, reflecting the presence of homologous fatty acid mixtures in the diglyceride moieties. In FIG. 6B, the peaks at m/z 674, 688, 702, 716 and 730 are assigned as a series of phosphatidylethanolamine adducts with potassium, containing total fatty acid composition of C28:0, C29:0, C30:0, C31:0 and C32:0 respectively. Other phosphatidylethanolamine species are observed with one double bond in a fatty acid moiety. These contribute ions at m/z 700, 714, and 728 corresponding to phosphatidylethanolamine (C30:1), phosphatidylethanolamine (C31:1) and phosphatidylethanolamine (C32:1). The ions at m/z 733, 747, and 761 are assigned as phosphatidylglycerol (C30:0), phosphatidylglycerol (C31:0) and phosphatidylglycerol (C32:0). The total fatty acid composition in three types of lipids is very similar. Similarities in fatty acid composition across lipid families in a given microorganism has been observed in other studies.[28]

Figure 7:
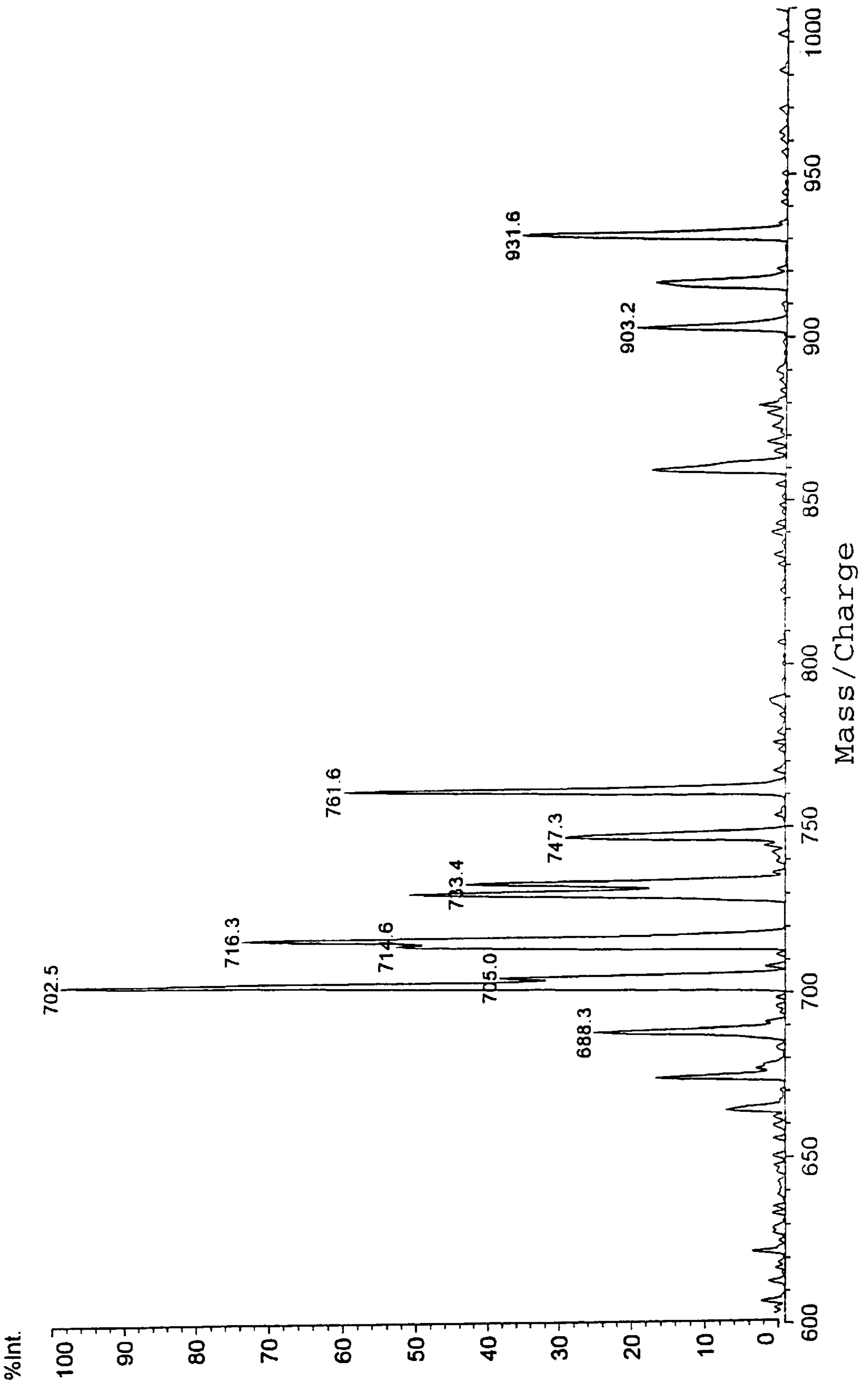
FIG. 7 shows Mass spectrum of *Bacillus thuringiensis* from a UV-matrix-assisted laser desorption/ionization TOF mass spectrometer.

The use of the cobalt/glycerol matrix for analysis of bacteria has been demonstrated at 337 nm irradiation and with a time-of-flight mass spectrometer. FIG. 7 shows a mass spectrum acquired on a UV-matrix-assisted laser desorption/ionization TOF mass spectrometer. The polar lipids detected from *B. thuringiensis* matched well in the spectra from the two mass spectrometers. Because the TOF spectrum was acquired in the linear mode, the resolution in the spectrum in FIG. 7 is lower. However, the comparison shows that the Co/glycerol matrix can be applied to bacterial analysis not only with different lasers but also with different analyzers.

Figure 8:
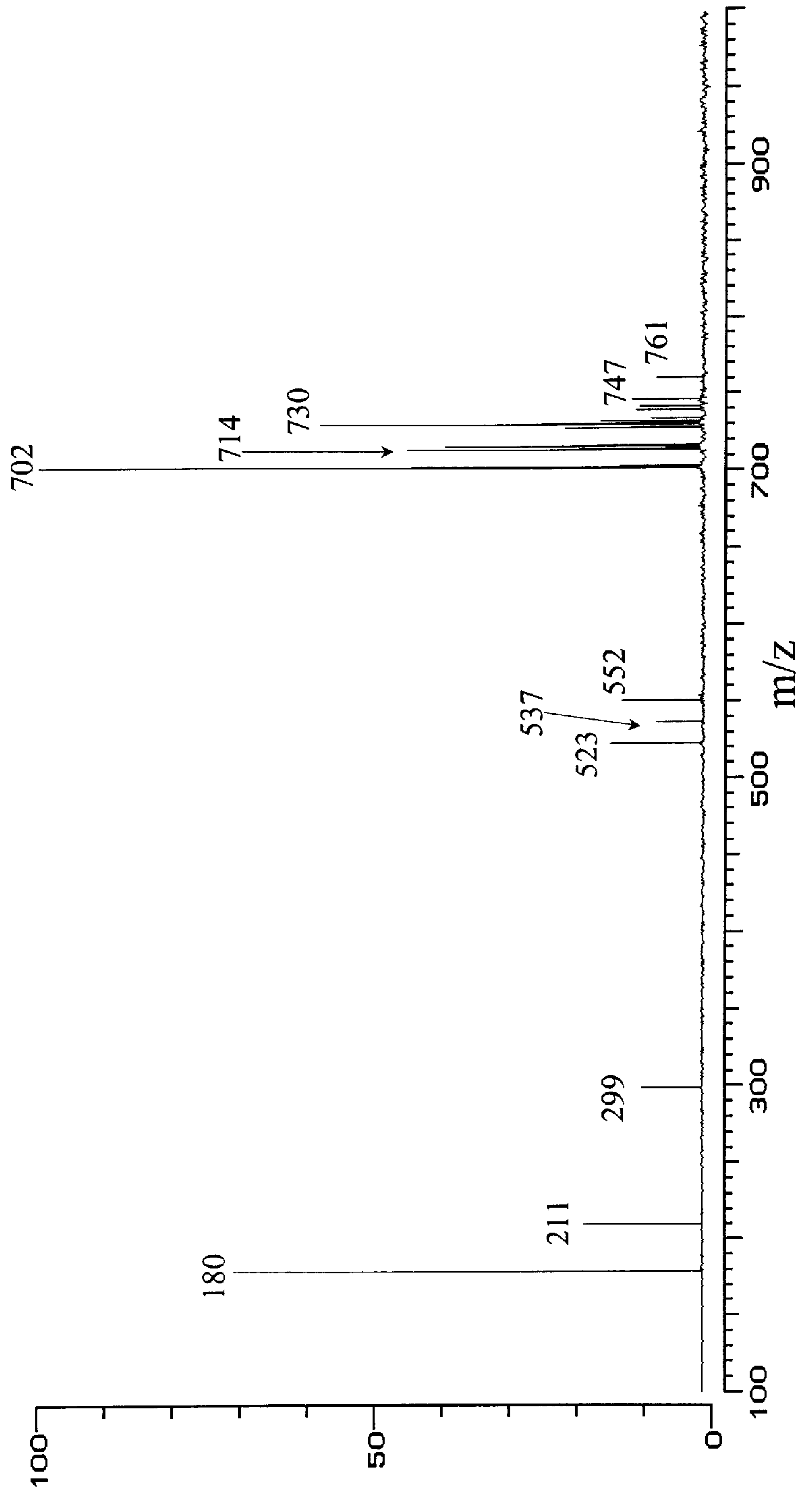
FIG. 8 shows Mass spectrum of *Bacillus sphaericus.*

FIG. 8 shows a mass spectrum acquired from *Bacillus sphaericus* on the FT-ICR instrument. The major peaks at 700, 714, 716, 728, 730 are kaliated phosphatidylethanolamine (C30:0), phosphatidylethanolamine (C31:1), phosphatidylethanolamine (C31:0), phosphatidylethanolamine (C32:1) and phosphatidylethanolamine (C32:0) respectively. The kaliated phosphatidylglycerol (C30:0), phosphatidylglycerol (C31:0) and phosphatidylglycerol (C32:0) at m/z 733, 747 and 761 are also observed. The peaks at m/z 523, 537 and 551 can be formed by loss of the polar head group from prontonated phosphatidylethanolamine (C30:0), phosphatidylethanolamine (C31:0), and phosphatidylethanolamine (C32:0) or protonated phosphatidylglycerol (C30:0), phosphatidylglycerol (C31:0) and phosphatidylglycerol (C32:0). These three fragments may also be formed by loss of neutral moiety (polar head+K) from (phosphatidylethanolamine+K) or (phosphatidylglycerol+K). Collisionally activated dissociation (CID) experiments with phosphatidylethanolamine indicate the fragment ions arising from the polar head group loss from (phosphatidylethanolamine+K) ion do not carry potassium. A comparison between the two species of Bacillus indicates similar phosphatidylethanolamine and phosphatidylglycerol components. However, the ratio of phosphatidylethanolamine to phosphatidylglycerol is different between these two species.

Figure 9:
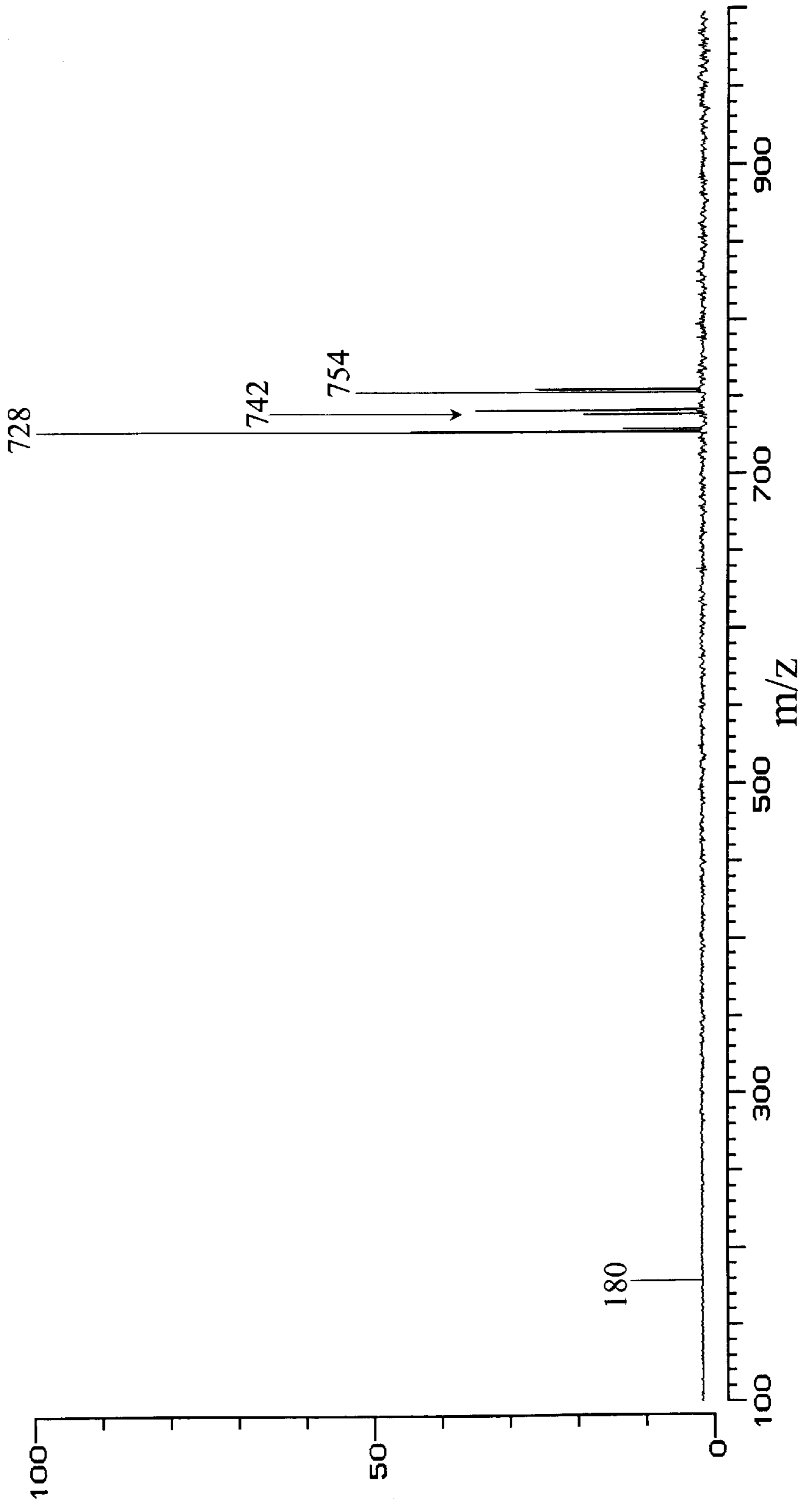
FIG. 9 shows Mass spectrum of *Erwinia herbicola.*
Figure 10:
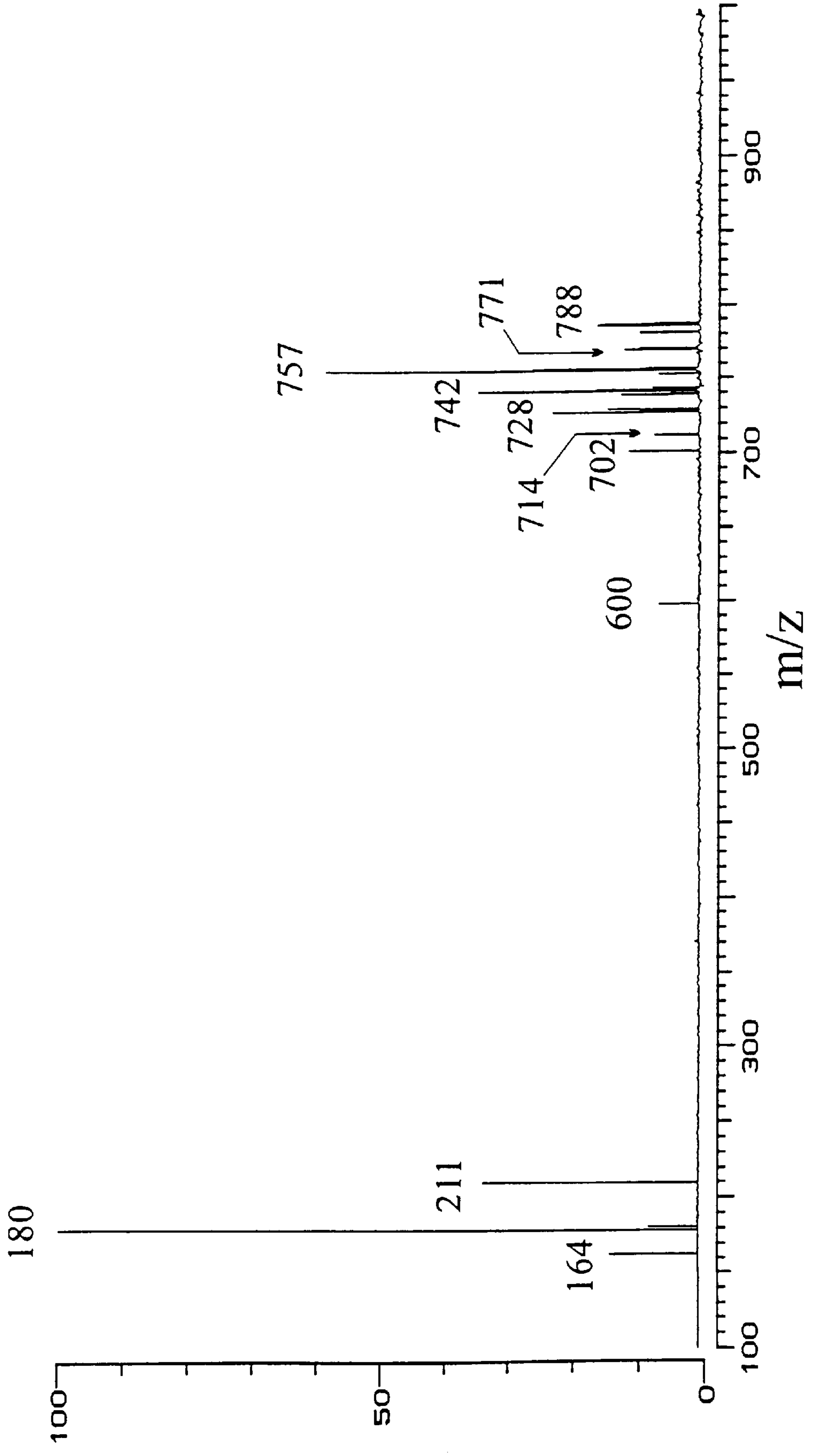
FIG. 10 shows Mass spectrum of *Escherichia coli.*

A mass spectrum from the Gram negative bacterium *Erwinia herbicola* is shown in FIG. 9. The mass peaks at m/z 728, 742, 754 and 756 are assigned as kaliated phosphatidylethanolamine (C32:1), phosphatidylethanolamine (C33:1), phosphatidylethanolamine (C34:2) and phosphatidylethanolamine (C34:1) respectively. In general, the outer cell wall of Gram negative bacteria contains higher levels of polar lipids than these of Gram positive species. In addition, phosphatidylethanolamine is usually present in much greater abundance than phosphatidylglycerol in Gram negative (but not Gram positive) species. A mass spectrum of *Escherichia coli* is shown in FIG. 10. Both phosphatidylethanolamine species and phosphatidylglycerol species are detected. The phosphatidylglycerol and phosphatidylethanolamine species observed in Co/glycerol spectra from the four bacteria are summarized in Table 1. Polar lipids in the two Gram-positive bacteria carry both saturated and unsaturated fatty acids, while phospholipids in the Gram-negative bacteria studied contain more unsaturated fatty acids. Fatty acid distribution in the cells are reported to vary according to the composition and temperature of the culture medium[29–30] However, the presence and relative abundances of specific polar lipid families in a given bacterium are less sensitive to growth conditions and lipid profiles and have been proposed as a first pass method to sort microorganisms by genus. The lipids that were desorbed from the four bacteria show different profiles, which may be used to distinguish them.

TABLE 1

PE and PG Species Desorbed from Bacteria

| total fatty acids | mass (M + K) PE | mass (M + K) PG | Gram positive: *B. thuringiensis* PE | *B. thuringiensis* PG | *B. sphaericus* PE | *B. sphaericus* PG | Gram negative: *E. herbicola* PE | *E. herbicola* PG | *E. coli* PE | *E. coli* PG |
|---|---|---|---|---|---|---|---|---|---|---|
| C28:0 | 674 | | x | | | | | | | |
| C29:0 | 688 | | x | | | | | | | |
| C30:0 | 702 | 733 | xx | x | xx | x | | | x | |
| C30:1 | 700 | | x | | | | | | | |
| C31:0 | 716 | 747 | x | x | x | x | | | | |
| C31:1 | 714 | | xx | | xx | | | | | |
| C32:0 | 730 | 761 | xx | x | xx | x | | | x | |
| C32:1 | 728 | | x | | x | | xx | | xx | |
| C33:1 | 742 | | | | | | xx | | xx | |
| C33:2 | 740 | 771 | | | | | | x | x | |
| C34:1 | 756 | 787 | | | | | x | | xx | x |
| C34:2 | 754 | | | | | | xx | | | |
| C35:1 | 770 | | | | | | | | x | |
| C36:2 | 782 | | | | | | | | x | |

x, ions observed in the mass spectra.
xx, three most abundant species observed.

The following references were cited herein.

(1) Karas, et al., *Int. J. Mass Spectrom. Ion Processes* 1987, 78, 53–68.

(2) Karas, M.; et al., *Anal. Chem.* 1988, 60, 2299–2301.

(3) Chait, B. T.; et al., *Science* 1992, 257, 1885–1894

(4) Beckey, H. D. *Principles of Field Ionization and Field Desorption Mass Spectrometry;* Pergamon Press: Oxford, 1977.

(5) Sundquist, B. U. R.; et al., Mass Spectrom. Rev. 1985, 4, 421. Grade, H.; et al., *J. Am. Chem. Soc.* 1978, 100, 5615.

(6) Cotter, R. *J. Anal. Chem. Acta.* 1987, 195, 45–59.

(7) Barber, M.; et al., *J. Chem. Soc., Chem. Commun.* 1981, 325.

(8) Fenselau, C.; et al., *Chem. Rev.* 1987, 87, 501–512.

(9) Zhao, S.; et al., *Anal. Chem.* 1991, 63, 450–453.

(10) Chan, T.-W. D.; et al., *J. Org. Mass Spectrom.* 1992, 27, 53–56.

(11) Yau, P. Y.; et al., *J. Chem. Phys. Letters.* 1993, 202, 93-

(12) Overberg, et al., *Rapid Commun. Mass Spectrom.* 1990, 4, 293–296.

(13) Overberg, et al., *Rapid Commun. Mass Spectrom.* 1991, 5, 128–131.

(14) Berkenkamp, S.; et al., *Rapid Commun. Mass Spectrom.* 1997, 11, 1399–1406.

(15) Cornett, D. S.; et al., *J. Anal. Chem.* 1993, 65, 2608–2613.

(16) Cornett, D. S.; et al., *J. Org. Mass Spectrom.* 1992, 27, 831–832.

(17) Williams, J. B.; et al., *Proceedings of the* 42nd *ASMS Conference on Mass Spectrometry and Allied Topics:* Chicago, Ill., May 29–Jun. 3, 1994; p 981.

(18) Tanaka, et al., *Rapid Commun. Mass Spectrom.* 1988, 2, 151–153.

(19) Hillenkamp, F.; et al., *Proceedings of the 45th ASMS Conference on Mass Spectrometry and Allied Topics:* Palm Spring, Calif., May 31–Jun. 5, 1997; p 1096; *Anal. Chem.* 1998, 70, in press.

(20) Sunner, J.; et al., *Anal. Chem.* 1995, 67, 4335–4342.

(21) Dale M. J.; et al., *Anal. Chem.* 1996, 68, 3321–3329.

(22) Dale, et al., *Rapid Commun. Mass Spectrom.* 1997, 11, 136–142.

(23) Zollner, P; et al., *Rapid Commun. Mass Spectrom.* 1996, 10, 1278–1282.

(24) Zöllner, P; et al., *Int. J. Mass Spectrom. Ion Processes* 1997, 169, 99–109.

(25) Heller, D. N.; et al., *Anal. Chem.* 1987, 59, 2806–2809.

(26) Heller, D. N.; et al., *Anal. Chem.* 1988, 60, 2787–2791.

(27) Fenselau, C.; et al., *Anal. Chem.* 1987, 59, 2806–2809.

(28) Koga, Y.; et al., *J Univ. of Occupational and Environmental Health* (*Japan*) 1982, 4, 227–240.

(29) Kates, M.; et al., *Can. J. of Biochem. and Physiol.* 1962, 40, 83–94.

(30) Shaw, N. *Adv. Appl. Microbiol.* 1974, 63–108.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of detecting biomarkers of microorganisms, comprising the steps of:

suspending a microorganism sample in a methanol:chloroform solution;

mixing said sample with a matrix comprising liquid(s) and light absorbing particles; and detecting biomarkers in microorganisms by utilizing mass spectrometry to said sample.

2. The method of claim 1, wherein said biomarkers are conjugated lipids.

3. The method of claim 2, wherein said conjugated lipids are selected from the group consisting of phosphatidylethanolamines, phosphatidylglycerols and diglycosyldiglycerides.

4. The method of claim 1, wherein said liquid is glycerol.

5. The method of claim 1, wherein said light absorbing particles are selected from the group consisting of cobalt particles and graphite particles.

6. The method of claim 1, wherein said mass spectrometry is selected from the group consisting of laser desorption mass spectrometry, matrix-assisted laser desorption ionization time-of-flight mass spectrometry and matrix-assisted laser desorption ionization Fourier-transform mass spectrometry.

* * * * *